US012057466B2

(12) United States Patent
Uchida et al.

(10) Patent No.: US 12,057,466 B2
(45) Date of Patent: Aug. 6, 2024

(54) DETECTION DEVICE AND DISPLAY DEVICE

(71) Applicant: Japan Display Inc., Tokyo (JP)

(72) Inventors: Makoto Uchida, Tokyo (JP); Takanori Tsunashima, Tokyo (JP)

(73) Assignee: Japan Display Inc., Tokyo (JP)

( * ) Notice: Subject to any disclaimer, the term of this patent is extended or adjusted under 35 U.S.C. 154(b) by 593 days.

(21) Appl. No.: 17/323,119

(22) Filed: May 18, 2021

(65) Prior Publication Data
US 2021/0273014 A1    Sep. 2, 2021

Related U.S. Application Data

(63) Continuation of application No. PCT/JP2019/043292, filed on Nov. 5, 2019.

(30) Foreign Application Priority Data

Nov. 22, 2018 (JP) .................................. 2018-219519

(51) Int. Cl.
*H01L 29/78* (2006.01)
*G06V 40/13* (2022.01)
(Continued)

(52) U.S. Cl.
CPC .... *H01L 27/14678* (2013.01); *G06V 40/1318* (2022.01); *H01L 27/14616* (2013.01);
(Continued)

(58) Field of Classification Search
CPC ......... H01L 27/14678; H01L 27/14616; H01L 29/78648; H01L 29/78675; H01L 29/7869;
(Continued)

(56) References Cited

U.S. PATENT DOCUMENTS

2005/0277293 A1* 12/2005 Kim .................... H01L 21/2885
257/E21.597
2014/0353470 A1* 12/2014 Kawanabe ........ H01L 27/14663
438/73

(Continued)

FOREIGN PATENT DOCUMENTS

JP    2014236162 A    12/2014
JP    2015-046873      3/2015

(Continued)

OTHER PUBLICATIONS

International Search Report mailed Jan. 28, 2020 in connection with PCT/JP2019/043292.

(Continued)

*Primary Examiner* — Sheikh Maruf
(74) *Attorney, Agent, or Firm* — K&L Gates LLP

(57) ABSTRACT

According to an aspect, a detection device includes: an insulating substrate; a plurality of photoelectric conversion elements that are arranged in a detection area of the insulating substrate, and each of which is configured to receive light and output a signal corresponding to the received light; a first switching element that is provided for each photoelectric conversion element and includes a first semiconductor, a source electrode, and a drain electrode; and an inorganic insulating layer provided between the photoelectric conversion element and the first switching element in a normal direction of the insulating substrate.

9 Claims, 11 Drawing Sheets

(51) Int. Cl.
*H01L 27/146* (2006.01)
*H01L 29/786* (2006.01)
*H10K 59/65* (2023.01)
*G06F 3/044* (2006.01)

(52) U.S. Cl.
CPC .. *H01L 29/78648* (2013.01); *H01L 29/78675* (2013.01); *H01L 29/7869* (2013.01); *H10K 59/65* (2023.02); *G06F 3/044* (2013.01)

(58) Field of Classification Search
CPC ............. H01L 27/1225; H01L 21/8234; H01L 27/088; H01L 27/14612; H01L 27/14643; G06V 40/1318; H10K 59/65; G06F 3/044; H04N 25/70; H04N 25/76; G09F 9/00; G09F 9/30
USPC .......................................................... 257/72
See application file for complete search history.

(56) References Cited

U.S. PATENT DOCUMENTS

| | | |
|---|---|---|
| 2015/0034831 A1 | 2/2015 | Miyake et al. |
| 2015/0234056 A1* | 8/2015 | Ofuji ................... A61B 6/4233 250/361 R |
| 2016/0014362 A1 | 1/2016 | Kurokawa |
| 2016/0337607 A1* | 11/2016 | Okamoto ............ H01L 27/1464 |
| 2017/0243909 A1 | 8/2017 | Kurokawa |
| 2018/0012069 A1* | 1/2018 | Chung ................ G06V 40/1394 |
| 2018/0076256 A1* | 3/2018 | Jiang ................... G06V 40/1324 |
| 2019/0170883 A1* | 6/2019 | Na ..................... H01L 27/14612 |
| 2020/0135796 A1* | 4/2020 | Kim .................. H01L 27/14612 |
| 2020/0219915 A1* | 7/2020 | Kim .................. H01L 27/14623 |
| 2020/0235091 A1* | 7/2020 | Kang .................. H01L 23/5225 |
| 2020/0294970 A1* | 9/2020 | Uh .......................... H01L 24/11 |
| 2020/0301029 A1* | 9/2020 | Na ..................... H01L 27/14689 |
| 2021/0175364 A1* | 6/2021 | Yoon ................. H01L 27/14609 |

FOREIGN PATENT DOCUMENTS

| | | |
|---|---|---|
| JP | 2015167221 A | 9/2015 |
| JP | 2016-028469 | 2/2016 |
| JP | 2016213471 A | 12/2016 |
| JP | 2017-153074 | 8/2017 |
| JP | 2018533749 A | 11/2018 |
| WO | 03/071342 | 8/2003 |

OTHER PUBLICATIONS

Japanese Office Action issued Sep. 27, 2022 in corresponding Japanese Application No. 2018-219519.
Chinese Office Action issued Jul. 20, 2022 in corresponding Chinese Application No. 201980076544.7.
Japanese Office Action issued Dec. 5, 2023 in corresponding Japanese Application No. 2023-031641.

* cited by examiner

DETECTION DEVICE AND DISPLAY DEVICE

CROSS-REFERENCE TO RELATED APPLICATION

This application claims the benefit of priority from Japanese Patent Application No. 2018-219519 filed on Nov. 22, 2018 and International Patent Application No. PCT/JP2019/043292 filed on Nov. 5, 2019, the entire contents of which are incorporated herein by reference.

BACKGROUND

1. Technical Field

What is disclosed herein relates to a detection device and a display device.

2. Description of the Related Art

In recent years, optical fingerprint sensors (refer, for example, to United States Patent Application Publication No. 2018/0012069 (US-A-2018/0012069)) are known as fingerprint sensors used, for example, for personal authentication. Such an optical fingerprint sensor includes a photoelectric conversion element that outputs a signal that changes with an amount of irradiating light. In the fingerprint sensor described in US-A-2018/0012069, a plurality of such photoelectric conversion elements, such as photodiodes, are arranged on a semiconductor substrate.

When thin-film transistors and various types of wiring are formed on an insulating substrate as a backplane for driving the photoelectric conversion elements, impurities may enter the thin-film transistors when the photoelectric conversion elements and electrodes are formed into a film. This may cause a reduction in reliability of the thin-film transistors.

SUMMARY

According to an aspect, a detection device includes: an insulating substrate; a plurality of photoelectric conversion elements that are arranged in a detection area of the insulating substrate, and each of which is configured to receive light and output a signal corresponding to the received light; a first switching element that is provided for each photoelectric conversion element and includes a first semiconductor, a source electrode, and a drain electrode; and an inorganic insulating layer provided between the photoelectric conversion element and the first switching element in a normal direction of the insulating substrate.

According to an aspect, a display device includes: the detection device described above; and a display panel that includes display elements to display an image and is disposed so as to face the detection device.

DETAILED DESCRIPTION

Figure 1:
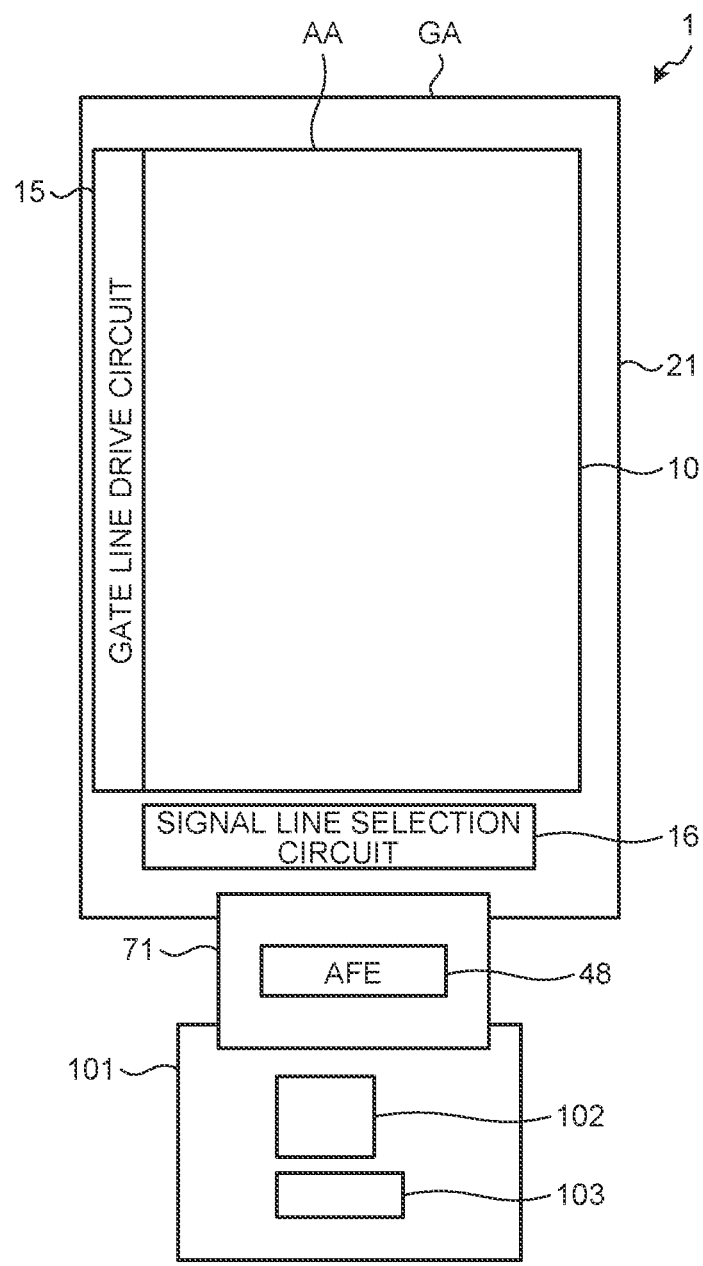
FIG. 1 is a plan view illustrating a detection device according to a first embodiment.

The following describes embodiments for carrying out the present invention in detail with reference to the drawings. The present invention is not limited to the description of the embodiments given below. Components described below include those easily conceivable by those skilled in the art or those substantially identical thereto. Moreover, the components described below can be appropriately combined. What is disclosed herein is merely an example, and the present invention naturally encompasses appropriate modifications easily conceivable by those skilled in the art while maintaining the gist of the invention. To further clarify the description, the drawings schematically illustrate, for example, widths, thicknesses, and shapes of various parts as compared with actual aspects thereof, in some cases. However, they are merely examples, and interpretation of the present invention is not limited thereto. The same element as that illustrated in a drawing that has already been discussed is denoted by the same reference numeral through the description and the drawings, and detailed description thereof will not be repeated in some cases where appropriate.

In this disclosure, when an element is described as being "on" another element, the element can be directly on the other element, or there can be one or more elements between the element and the other element.

First Embodiment

Figure 2:
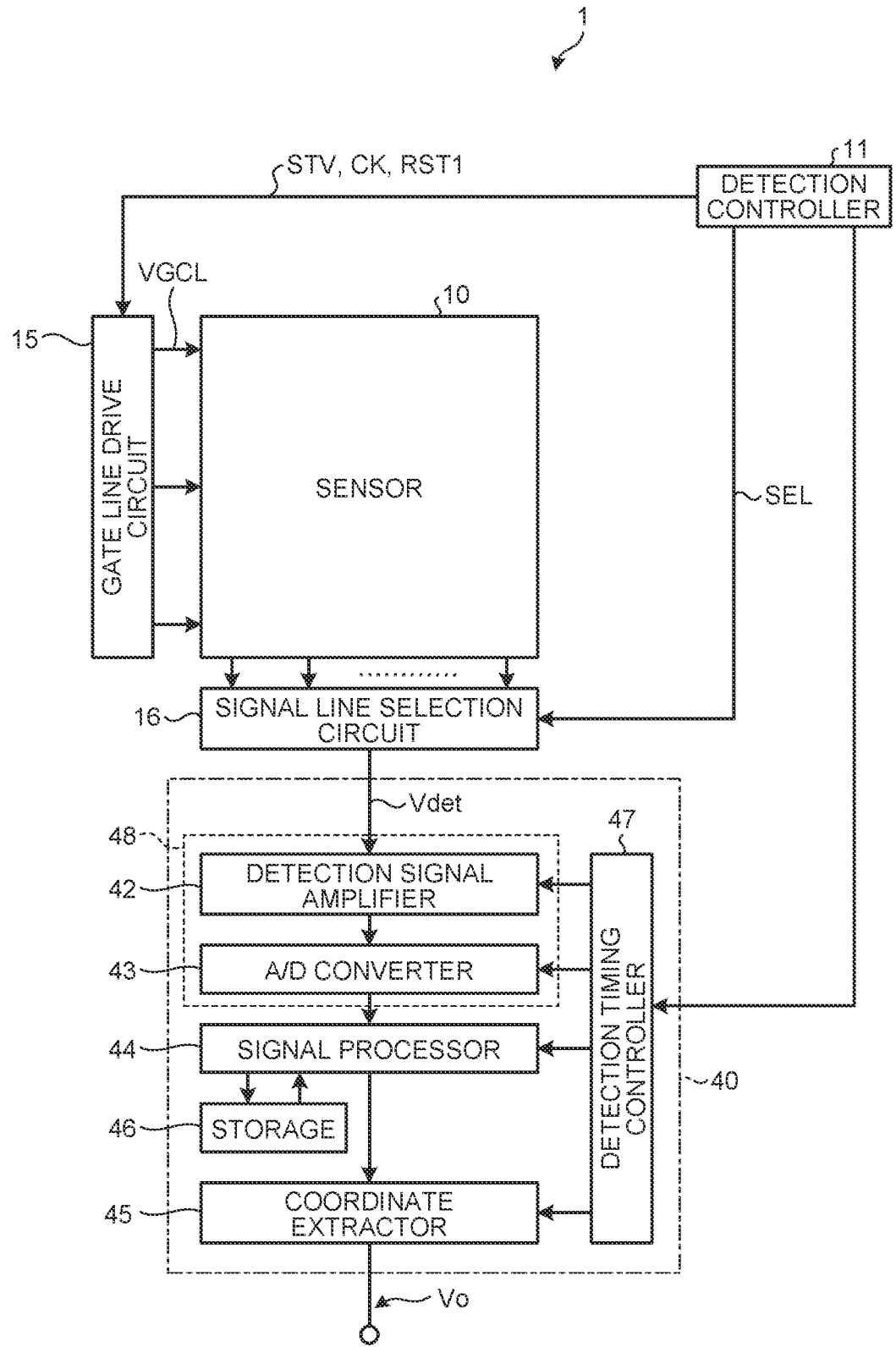
FIG. 2 is a block diagram illustrating a configuration example of the detection device according to the first embodiment.

FIG. 1 is a plan view illustrating a detection device according to a first embodiment. FIG. 2 is a block diagram illustrating a configuration example of the detection device according to the first embodiment. As illustrated in FIG. 1, a detection device 1 includes an insulating substrate 21, a sensor 10, a gate line drive circuit 15, a signal line selection circuit 16, an analog front-end circuit (hereinafter, called "AFE") 48, a control circuit 102, and a power supply circuit 103.

As illustrated in FIG. 1, a control board 101 is electrically coupled to the insulating substrate 21 through a flexible printed circuit board 71. The flexible printed circuit board 71 is provided with the AFE 48. The control board 101 is provided with the control circuit 102 and the power supply circuit 103. The control circuit 102 is, for example, a field programmable gate array (FPGA). The control circuit 102 supplies control signals to the sensor 10, the gate line drive circuit 15, and the signal line selection circuit 16 to control a detection operation of the sensor 10. The power supply circuit 103 supplies voltage signals including a power supply signal SVS (refer to FIG. 4) to the sensor 10 and the gate line drive circuit 15.

As illustrated in FIG. 1, the insulating substrate 21 has a detection area AA and a peripheral area GA. The detection area AA is an area overlapping a plurality of photodiodes PD (refer to FIG. 4) included in the sensor 10. The peripheral area GA is an area outside the detection area AA, and is an area not overlapping the photodiodes PD. That is, the peripheral area GA is an area between the outer circumference of the detection area AA and the edges of the insulating substrate 21. The gate line drive circuit 15 and the signal line selection circuit 16 are provided in the peripheral area GA.

As illustrated in FIG. 2, the detection device 1 further includes a detection controller 11 and a detector 40. The control circuit 102 includes some or all functions of the detection controller 11. The control circuit 102 also includes some or all functions of the detector 40 except those of the AFE 48.

The sensor 10 is an optical sensor including the photodiodes PD serving as photoelectric conversion elements. Each of the photodiodes PD included in the sensor 10 outputs an electrical signal corresponding to light emitted thereto as a detection signal Vdet to the signal line selection circuit 16. The sensor 10 performs the detection in response to a gate drive signal VGCL supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals including a start signal STV, a clock signal CK, and a reset signal RST1 to the gate line drive circuit 15. The detection controller 11 also supplies various control signals including a selection signal SEL to the signal line selection circuit 16.

The gate line drive circuit 15 drives a plurality of gate lines GCL (refer to FIG. 3) based on the various control signals. The gate line drive circuit 15 sequentially or simultaneously selects the gate lines GCL and supplies the gate drive signals VGCL to the selected gate lines GCL. Through this operation, the gate line drive circuit 15 selects the photodiodes PD coupled to the gate lines GCL.

Figure 3:
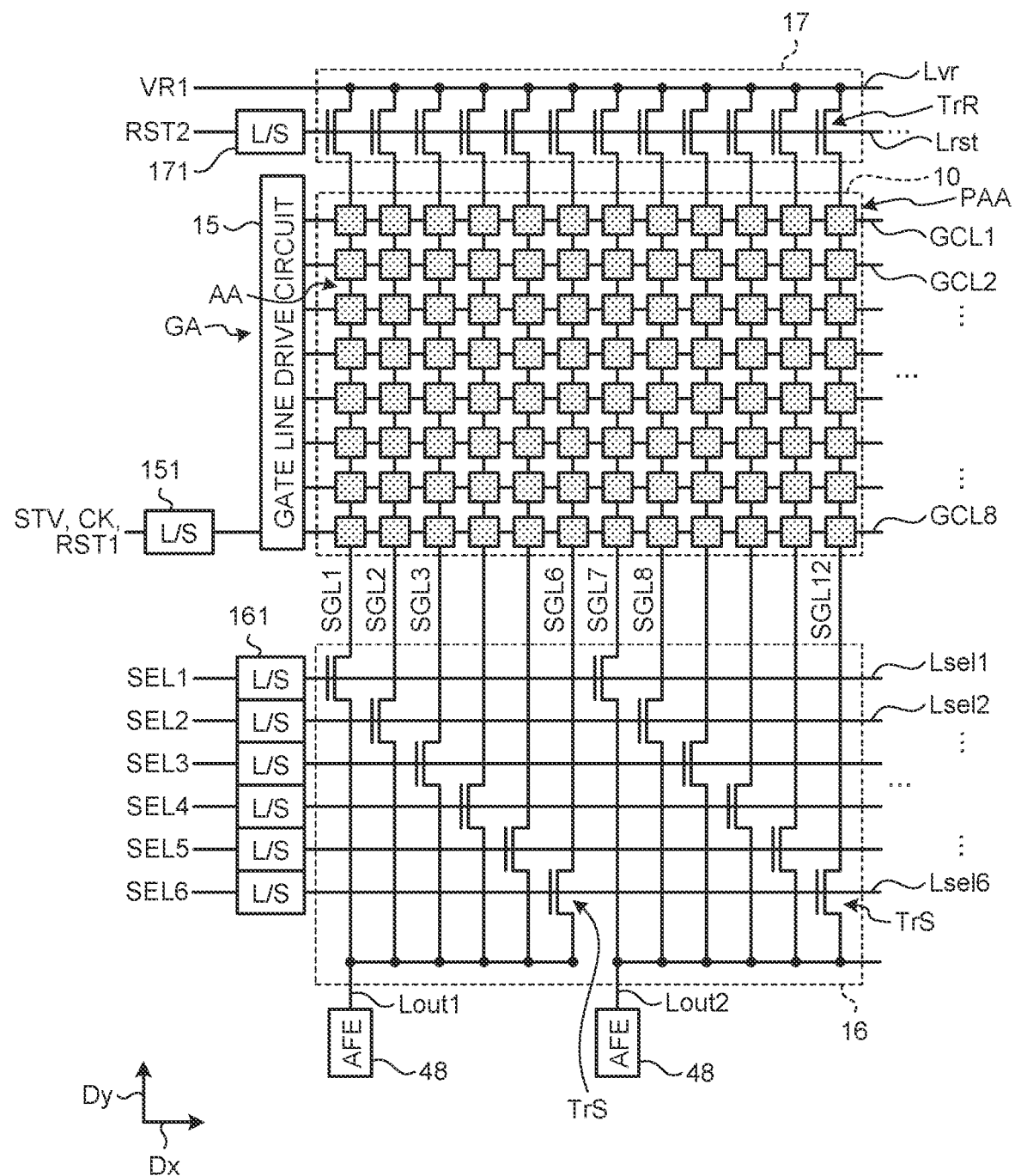
FIG. 3 is a circuit diagram illustrating the detection device.

The signal line selection circuit 16 is a switch circuit that sequentially or simultaneously selects a plurality of signal lines SGL (refer to FIG. 3). The signal line selection circuit 16 couples the selected signal lines SGL to the AFE 48 based on the selection signal SEL supplied from the detection controller 11. Through this operation, the signal line selection circuit 16 outputs the detection signal Vdet of each of the photodiodes PD to the detector 40. The signal line selection circuit 16 is, for example, a multiplexer.

The detector 40 includes the AFE 48, a signal processor 44, a coordinate extractor 45, a storage 46, and a detection timing controller 47. The detection timing controller 47 controls, based on a control signal supplied from the detection controller 11, the AFE 48, the signal processor 44, and the coordinate extractor 45 such that they operate in synchronization with one another.

The AFE 48 is a signal processing circuit having functions of at least a detection signal amplifier 42 and an analog-to-digital (A/D) converter 43. The detection signal amplifier 42 amplifies the detection signal Vdet. The A/D converter 43 converts an analog signal output from the detection signal amplifier 42 into a digital signal.

The signal processor 44 is a logic circuit that detects, based on an output signal of the AFE 48, a predetermined physical quantity received by the sensor 10. When a finger is in contact with or in proximity to a detection surface, the signal processor 44 can detect asperities of a surface of the finger or a palm based on the signal from the AFE 48.

The storage 46 temporarily stores a signal calculated by the signal processor 44. The storage 46 may be, for example, a random-access memory (RAM) or a register circuit.

The coordinate extractor 45 is a logic circuit that obtains detected coordinates of the asperities of the surface of, for example, the finger when the contact or the proximity of the finger is detected by the signal processor 44. The coordinate extractor 45 combines the detection signals Vdet output from the respective photodiodes PD of the sensor 10 to generate two-dimensional information representing a shape of the asperities of the surface of, for example, the finger. The coordinate extractor 45 may output the detection signals Vdet as sensor outputs Vo, without calculating the detected coordinates.

Figure 4:
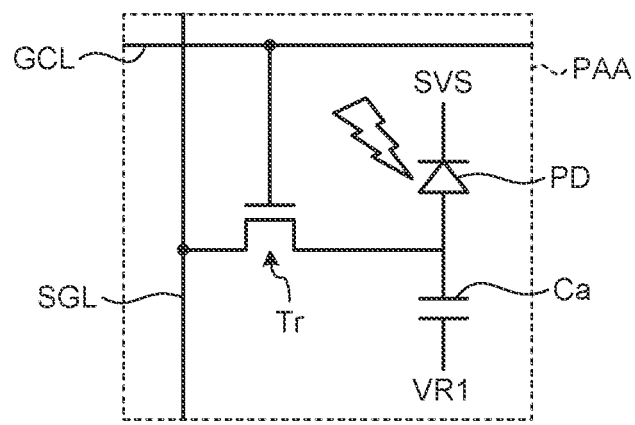
FIG. 4 is a circuit diagram illustrating a partial detection area.
Figure 5:
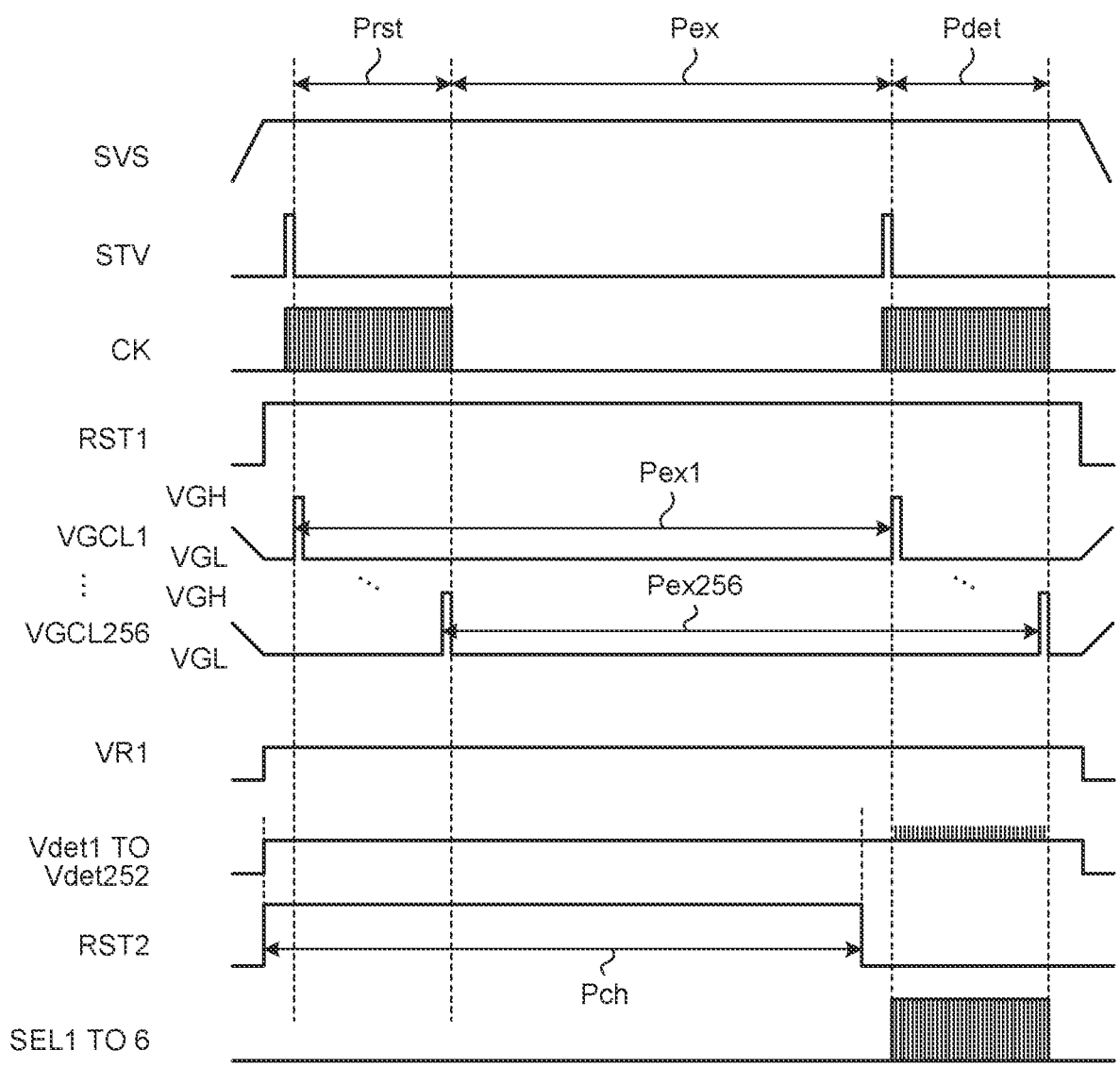
FIG. 5 is a timing waveform diagram illustrating an operation example of the detection device.

The following describes a circuit configuration example and an operation example of the detection device 1. FIG. 3 is a circuit diagram illustrating the detection device. FIG. 4 is a circuit diagram illustrating a partial detection area. FIG. 5 is a timing waveform diagram illustrating the operation example of the detection device.

As illustrated in FIG. 3, the sensor 10 has a plurality of partial detection areas PAA arranged in a matrix having a row-column configuration. As illustrated in FIG. 4, each of the partial detection areas PAA includes the photodiode PD, a capacitive element Ca, and a first switching element Tr. The first switching element Tr is provided corresponding to the photodiode PD. The first switching element Tr includes a thin-film transistor, and in this example, includes an n-channel metal oxide semiconductor (MOS) thin-film transistor (TFT). The gate of the first switching element Tr is coupled to each of the gate lines GCL. The source of the first switching element Tr is coupled to each of the signal lines SGL. The drain of the first switching element Tr is coupled to the anode of the photodiode PD and the capacitive element Ca.

The cathode of the photodiode PD is supplied with the power supply signal SVS from the power supply circuit 103. The capacitive element Ca is supplied with a reference signal VR1 serving as an initial potential of the capacitive element Ca from the power supply circuit 103.

When the partial detection area PAA is irradiated with light, a current corresponding to an amount of the light flows through the photodiode PD. As a result, an electrical charge is stored in the capacitive element Ca. After the first switching element Tr is turned on, a current corresponding to the electrical charge stored in the capacitive element Ca flows through the signal line SGL. The signal line SGL is coupled to the AFE 48 through the signal line selection circuit 16. Thus, the detection device 1 can detect a signal corresponding to the amount of the light emitted to the photodiode PD for each of the partial detection areas PAA.

As illustrated in FIG. 3, the gate lines GCL extend in a first direction Dx and are coupled to the partial detection areas PAA arranged in the first direction Dx. A plurality of gate lines GCL1, GCL2, . . . , GCL8 are arranged in a second direction Dy and are each coupled to the gate line drive circuit 15. In the following description, the gate lines GCL1, GCL2, . . . , GCL8 will each be simply referred to as the gate line GCL when need not be distinguished from one another.

Although the number of the gate lines GCL is eight, this is merely an example. Eight or more, such as 256, of the gate lines GCL may be arranged.

The first direction Dx is a direction in a plane parallel to the insulating substrate 21 and is, for example, a direction parallel to the gate lines GCL. The second direction Dy is a direction in a plane parallel to the insulating substrate 21 and is, for example, a direction orthogonal to the first direction Dx. The second direction Dy may intersect the first direction Dx without being orthogonal thereto. The normal direction of the insulating substrate 21 is a direction orthogonal to the first direction Dx and the second direction Dy.

The signal lines SGL extend in the second direction Dy and are coupled to the partial detection areas PAA arranged in the second direction Dy. A plurality of signal lines SGL1, SGL2, . . . , SGL12 are arranged in the first direction Dx and are each coupled to the signal line selection circuit 16 and a reset circuit 17. Although the number of the signal lines SGL is 12, this is merely an example. Twelve or more, such as 252, of the signal lines SGL may be arranged. In FIG. 3, the sensor 10 is provided between the signal line selection circuit 16 and the reset circuit 17. The present disclosure is not limited thereto. The signal line selection circuit 16 and the reset circuit 17 may be coupled to the same ends of the signal lines SGL.

The gate line drive circuit 15 receives the various control signals such as the start signal STV, the clock signal CK, and the reset signal RST1 through a level shifter 151. The gate line drive circuit 15 includes a plurality of second switching elements TrG (refer to FIG. 7). The gate line drive circuit 15 sequentially selects the gate lines GCL1, GCL2, . . . , GCL8 in a time-division manner by operations of the second switching elements TrG. The gate line drive circuit 15 supplies the gate drive signals VGCL to the first switching elements Tr through the selected gate lines GCL. This operation selects the partial detection areas PAA arranged in the first direction Dx as detection targets.

The signal line selection circuit 16 includes a plurality of selection signal lines Lsel, a plurality of output signal lines Lout, and third switching elements TrS. The third switching elements TrS are provided corresponding to the signal lines SGL. Six of the signal lines SGL1, SGL2, . . . , SGL6 are coupled to a common output signal line Lout1. Six of the signal lines SGL7, SGL8, . . . , SGL12 are coupled to a common output signal line Lout2. The output signal lines Lout1 and Lout2 are each coupled to the AFE 48.

The signal lines SGL1, SGL2, . . . , SGL6 are grouped into a first signal line block, and the signal lines SGL7, SGL8, . . . , SGL12 are grouped into a second signal line block. The selection signal lines Lsel are coupled to the gates of the respective third switching elements TrS included in one of the signal line blocks. One of the selection signal lines Lsel is coupled to the gates of the third switching elements TrS in the signal line blocks. Specifically, selection signal lines Lsel1, Lsel2, . . . , Lsel6 are respectively coupled to the third switching elements TrS corresponding to the signal lines SGL1, SGL2, . . . , SGL6. The selection signal line Lsel1 is coupled to the third switching element TrS corresponding to the signal line SGL1 and the third switching element TrS corresponding to the signal line SGL7. The selection signal line Lsel2 is coupled to the third switching element TrS corresponding to the signal line SGL2 and the third switching element TrS corresponding to the signal line SGL8.

The control circuit 102 (refer to FIG. 1) sequentially supplies the selection signals SEL to the selection signal lines Lsel through level shifters 161. This operation causes the signal line selection circuit 16 to operate the third switching elements TrS to sequentially select the signal lines SGL in each of the signal line blocks in a time-division manner. The signal line selection circuit 16 simultaneously selects one signal line SGL in each of the signal line blocks. With the above-described configuration, the detection device 1 can reduce the number of integrated circuits (ICs) including the AFE 48 or the number of terminals of the ICs.

As illustrated in FIG. 3, the reset circuit 17 includes a reference signal line Lvr, a reset signal line Lrst, and fourth switching elements TrR. The fourth switching elements TrR are provided corresponding to the signal lines SGL. The reference signal line Lvr is coupled to either the sources or the drains of the fourth switching elements TrR. The reset signal line Lrst is coupled to the gates of the fourth switching elements TrR.

The control circuit 102 supplies a reset signal RST2 to the reset signal line Lrst through a level shifter 171. This operation turns on the fourth switching elements TrR to electrically couple the signal lines SGL to the reference signal line Lvr. The power supply circuit 103 supplies the reference signal VR1 to the reference signal line Lvr. This operation supplies the reference signal VR1 to the capacitive elements Ca included in the partial detection areas PAA.

As illustrated in FIG. 5, the detection device 1 includes a reset period Prst, an exposure period Pex, and a reading period Pdet. The power supply circuit 103 supplies the power supply signal SVS to the cathode of the photodiode PD through the reset period Prst, the exposure period Pex, and the reading period Pdet. The control circuit 102 supplies the reference signal VR1 and the reset signal RST2 serving as high-level voltage signals to the reset circuit 17 from a time before the reset period Prst starts. The control circuit 102 supplies the start signal STV to the gate line drive circuit 15, and the reset period Prst starts.

During the reset period Prst, a shift register included in the gate line drive circuit 15 sequentially selects each of the gate lines GCL based on the start signal STV, the clock signal CK, and the reset signal RST1. The gate line drive circuit 15 sequentially supplies the gate drive signals VGCL to the gate lines GCL. The gate drive signal VGCL has a pulsed waveform having a high-level voltage VGH and a low-level voltage VGL. In FIG. 5, 256 gate lines GCL are provided, and gate drive signals VGCL1, . . . , VGCL256 are sequentially supplied to the gate lines GCL.

Thus, during the reset period Prst, the capacitive elements Ca of all the partial detection areas PAA are sequentially electrically coupled to the signal lines SGL and are supplied with the reference signal VR1. As a result, capacitances of the capacitive elements Ca are reset.

After the gate drive signal VGCL256 is supplied to the gate line GCL, the exposure period Pex starts. The start timing and end timing of actual exposure periods Pex1, . . . , Pex256 in the partial detection areas PAA corresponding to the gate lines GCL differ from one another. Each of the exposure periods Pex1, . . . , Pex256 starts at a time when the gate drive signal VGCL changes from the high-level voltage VGH to the low-level voltage VGL during the reset period Prst. Each of the exposure periods Pex1, . . . , Pex256 ends at a time when the gate drive signal VGCL changes from the low-level voltage VGL to the high-level voltage VGH during the reading period Pdet. The lengths of exposure time of the exposure periods Pex1, . . . , Pex256 are equal.

During the exposure period Pex, the current corresponding to the light emitted to the photodiode PD flows in each of the partial detection areas PAA. As a result, the electrical charge is stored in each of the capacitive elements Ca.

At a time before the reading period Pdet starts, the control circuit 102 sets the reset signal RST2 to a low-level voltage. This operation stops the operation of the reset circuit 17. During the reading period Pdet, the gate line drive circuit 15 sequentially supplies the gate drive signals VGCL1, . . . , VGCL256 to the gate lines GCL in the same manner as during the reset period Prst.

For example, during a period in which the gate drive signal VGCL1 is at the high-level voltage VGH, the control circuit 102 sequentially supplies selection signals SEL1, . . . , SEL6 to the signal line selection circuit 16. With this operation, the signal lines SGL for the partial detection areas PAA selected by the gate drive signal VGCL1 are sequentially or simultaneously coupled to the AFE 48. As a result, the detection signal Vdet is supplied to the AFE 48. In the same manner, the signal line selection circuit 16 sequentially selects the signal line SGL in each period in which a corresponding one of the gate drive signals VGCL is set to the high-level voltage VGH. Thus, the detection device 1 can output the detection signals Vdet of all the partial detection areas PAA to the AFE 48 during the reading period Pdet.

The detection device 1 may perform the fingerprint detection by repeatedly performing the processing during the reset period Prst, the exposure period Pex, and the reading period Pdet. Alternatively, the detection device 1 may start the detection operation when having detected that a finger, for example, is in contact with or in proximity to the detection surface.

Figure 6:
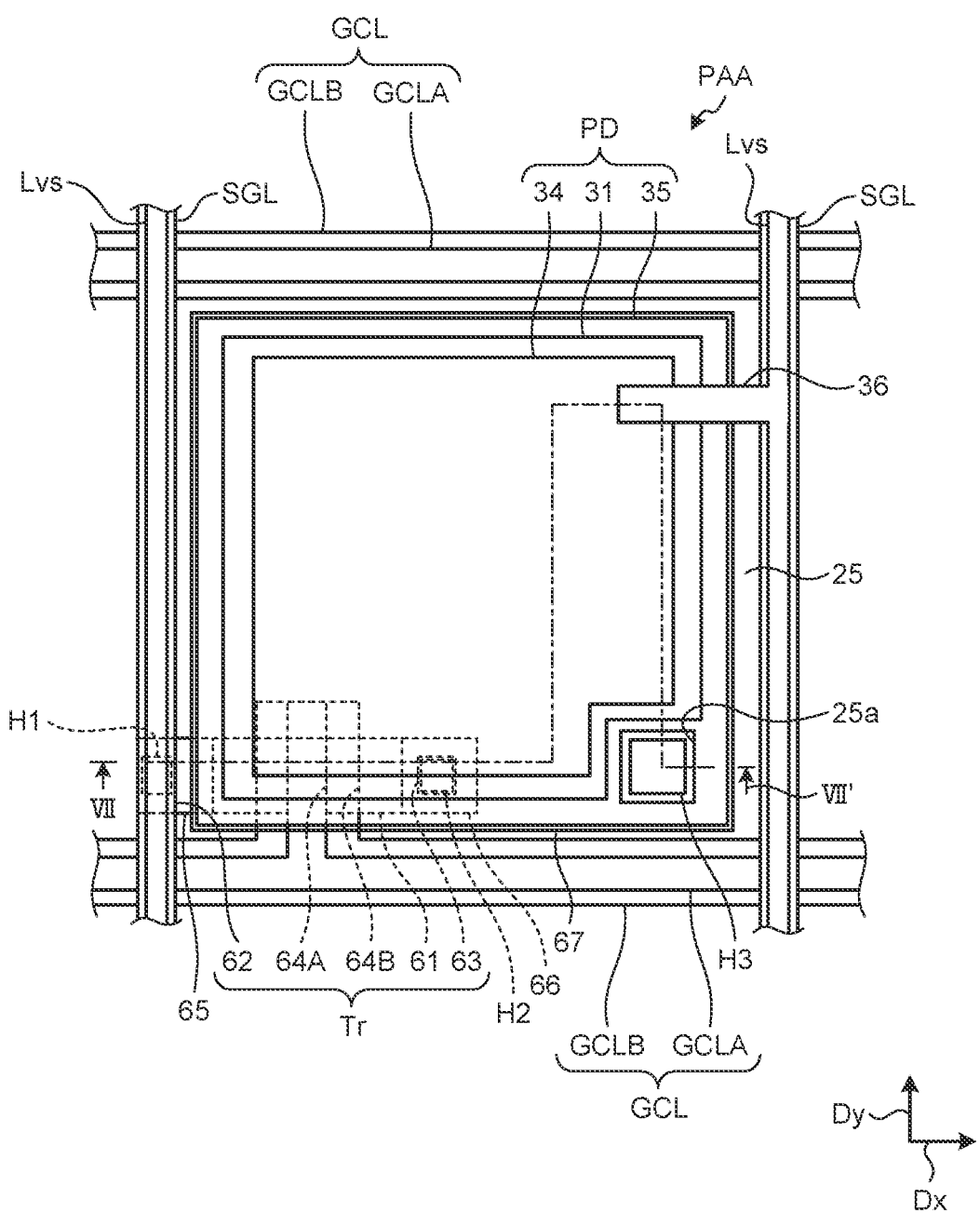
FIG. 6 is a plan view schematically illustrating the partial detection area of the detection device according to the first embodiment.
Figure 7:
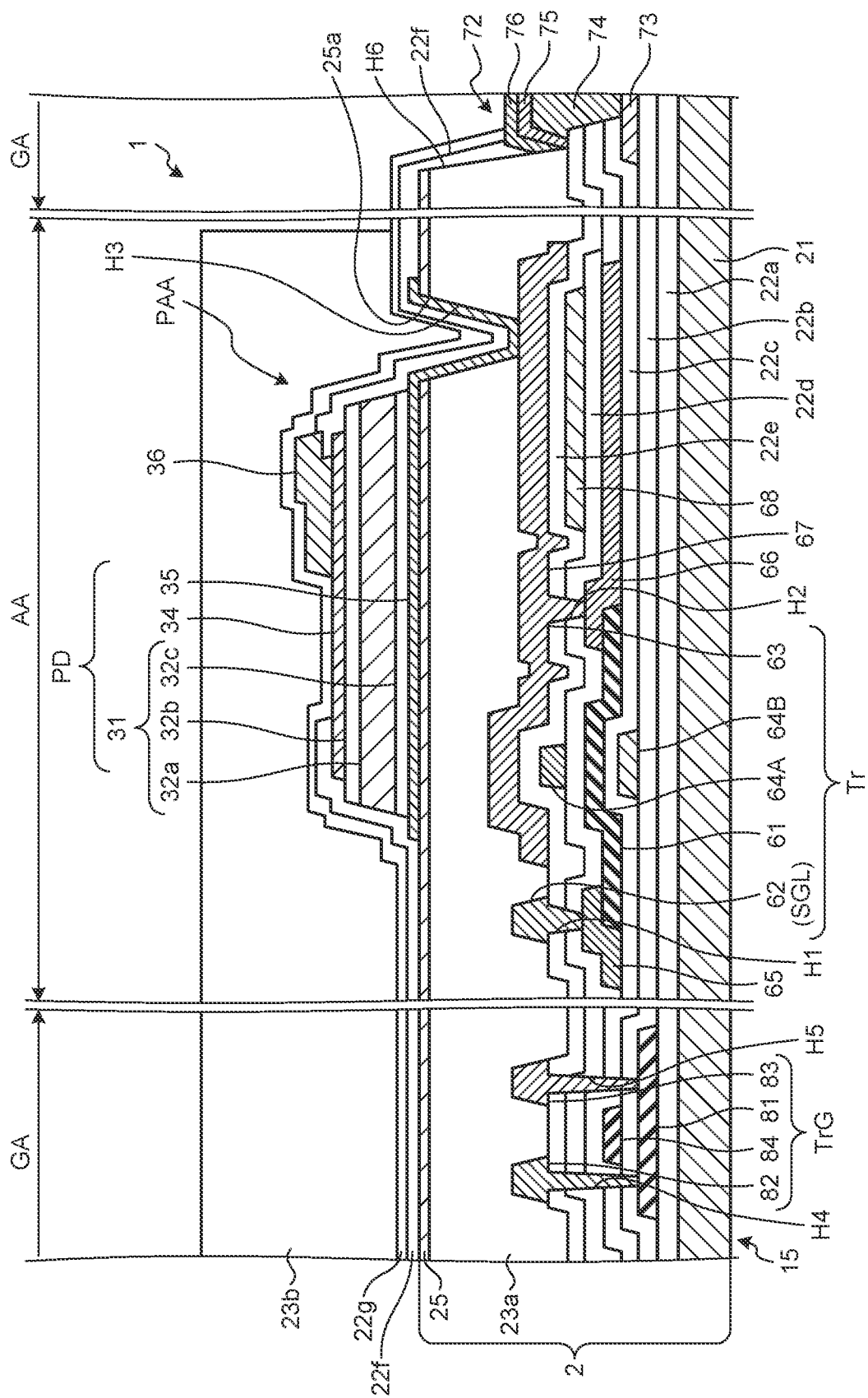
FIG. 7 is a sectional view taken along line VII-VII' of FIG. 6.

The following describes a detailed configuration of the detection device 1. FIG. 6 is a plan view schematically illustrating the partial detection area of the detection device according to the first embodiment. FIG. 7 is a sectional view taken along line VII-VII' of FIG. 6. To illustrate a relation between a layered structure of the detection area AA and a layered structure of the peripheral area GA, FIG. 7 illustrates the section taken along line VII-VII' and a section of a portion of the peripheral area GA including one of the second switching elements TrG in a schematically connected manner. FIG. 7 also illustrates a section of a portion of the peripheral area GA including a terminal portion 72 in a schematically connected manner.

In the description of the detection device 1, in a direction orthogonal to a surface of the insulating substrate 21, the term "above (upper side)" refers to a direction from the insulating substrate 21 toward the photodiode PD, and the term "below (lower side)" refers to a direction from the photodiode PD toward the insulating substrate 21. The term "plan view" refers to a case of viewing from the direction orthogonal to the surface of the insulating substrate 21.

As illustrated in FIG. 6, the partial detection area PAA is an area surrounded by the gate lines GCL and the signal lines SGL. In the present embodiment, the gate line GCL includes a first gate line GCLA and a second gate line GCLB. The first gate line GCLA is provided so as to overlap the second gate line GCLB. The first gate line GCLA and the second gate line GCLB are provided in different layers with insulating layers (a fifth inorganic insulating layer 22c and a sixth inorganic insulating layer 22d (refer to FIG. 7)) interposed therebetween. The first gate line GCLA and the second gate line GCLB are electrically coupled to each other at any place and are supplied with the gate drive signals VGCL having the same potential. At least one of the first gate line GCLA and the second gate line GCLB is coupled to the gate line drive circuit 15. In FIG. 6, the first gate line GCLA has a different width from that of the second gate line GCLB. However, the first gate line GCLA may have the same width as that of the second gate line GCLB.

The photodiode PD is provided in the area surrounded by the gate lines GCL and the signal lines SGL. The photodiode PD includes a third semiconductor 31, an upper electrode 34, and a lower electrode 35. The photodiode PD is, for example, a positive-intrinsic-negative (PIN) photodiode.

As illustrated in FIG. 6, the upper electrode 34 is coupled to a power supply signal line Lvs through coupling wiring 36. The power supply signal line Lvs is wiring that supplies the power supply signal SVS to the photodiode PD. In the present embodiment, the power supply signal line Lvs extends in the second direction Dy so as to overlap the signal line SGL. The partial detection areas PAA arranged in the second direction Dy are coupled to the common power supply signal line Lvs. Such a configuration allows the partial detection area PAA to have a larger opening. The lower electrode 35, the third semiconductor 31, and the upper electrode 34 have a quadrilateral shape in the plan view. However, the shape of the lower electrode 35, the third semiconductor 31, and the upper electrode 34 is not limited thereto, and can be changed as appropriate.

The first switching element Tr is provided near an intersecting portion between the gate line GCL and the signal line SGL. The first switching element Tr includes a first semiconductor 61, a source electrode 62, a drain electrode 63, a first gate electrode 64A, and a second gate electrode 64B.

The first semiconductor 61 is an oxide semiconductor. The first semiconductor 61 is more preferably a transparent amorphous oxide semiconductor (TAOS) among types of the oxide semiconductor. Using the oxide semiconductor as the first switching element Tr can reduce a leakage current of the first switching element Tr. That is, the first switching element Tr can reduce the leakage current from the partial detection area PAA that is not selected during the reading period Pdet illustrated in FIG. 5. As a result, the detection device 1 can increase a signal-to-noise (S/N) ratio.

The first semiconductor 61 is provided along the first direction Dx and intersects the first gate electrode 64A and the second gate electrode 64B in a plan view. The first gate electrode 64A and the second gate electrode 64B are provided so as to branch from the first gate line GCLA and the second gate line GCLB, respectively. In other words, portions of the first gate line GCLA and the second gate line GCLB overlapping the first semiconductor 61 serve as the first gate electrode 64A and the second gate electrode 64B. Aluminum (Al), copper (Cu), silver (Ag), molybdenum (Mo), or an alloy of these materials is used as the first gate electrode 64A and the second gate electrode 64B. A channel area is formed at a portion of the first semiconductor 61 overlapping the first gate electrode 64A and the second gate electrode 64B.

One end of the first semiconductor 61 is coupled to the source electrode 62 through a contact hole H1. The other end of the first semiconductor 61 is coupled to the drain electrode 63 through a contact hole H2. A portion of the signal line SGL overlapping the first semiconductor 61 serves as the source electrode 62. A portion of a third conductive layer 67 overlapping the first semiconductor 61 serves as the drain electrode 63. The third conductive layer 67 is coupled to the lower electrode 35 through a contact hole H3. The above-described configuration allows the first switching element Tr to switch between coupling and decoupling of the photodiode PD to and from the signal line SGL.

The following describes a layer configuration of the first switching element Tr and the photodiode PD. As illustrated in FIG. 7, the photodiode PD is provided on the upper side of a backplane 2. The backplane 2 is a drive circuit board that drives the sensor on a per predetermined partial detection area PAA basis. The backplane 2 includes the insulating substrate 21, and the first switching element Tr, the second switching element TrG, and various types of wiring provided on the insulating substrate 21.

The first switching element Tr is provided on the insulating substrate 21. The insulating substrate 21 is, for example, a glass substrate. Alternatively, the insulating substrate 21 may be a resin substrate or a resin film formed of a resin such as polyimide. In the detection device 1, the first switching element Tr including the oxide semiconductor is formed above the insulating substrate 21. This configuration allows the detection device 1 to have an area of the detection area AA larger than that in a case of using a semiconductor substrate such as a silicon substrate.

The second gate electrode 64B is provided above the insulating substrate 21 with a third inorganic insulating layer 22a and a fourth inorganic insulating layer 22b interposed therebetween. For example, a silicon oxide (SiO) film, a silicon nitride (SiN) film, or a silicon oxynitride (SiON) film is used as each of the third to a ninth inorganic insulating layers 22a to 22g. Each of the inorganic insulating layers is not limited to a single layer, but may be a multilayered film.

The fifth inorganic insulating layer 22c is provided on the upper side of the fourth inorganic insulating layer 22b so as to cover the second gate electrode 64B. The first semiconductor 61, a first conductive layer 65, and a second conductive layer 66 are provided on the upper side of the fifth inorganic insulating layer 22c. The first conductive layer 65 is provided so as to cover an end of the first semiconductor 61 coupled to the source electrode 62. The second conductive layer 66 is provided so as to cover an end of the first semiconductor 61 coupled to the drain electrode 63.

The sixth inorganic insulating layer 22d is provided above the fifth inorganic insulating layer 22c so as to cover the first semiconductor 61, the first conductive layer 65, and the second conductive layer 66. The first gate electrode 64A is provided above the sixth inorganic insulating layer 22d. The first semiconductor 61 is provided between the first gate electrode 64A and the second gate electrode 64B in a direction orthogonal to the insulating substrate 21. That is, the first switching element Tr has what is called a dual-gate structure. However, the first switching element Tr may have a top-gate structure in which the first gate electrode 64A is provided while the second gate electrode 64B is not provided, or a bottom-gate structure in which only the second gate electrode 64B is provided without the first gate electrode 64A being provided.

The seventh inorganic insulating layer 22e is provided on the upper side of the sixth inorganic insulating layer 22d so as to cover the first gate electrode 64A. The source electrode 62 (signal line SGL) and the drain electrode 63 (third conductive layer 67) are provided on the upper side of the seventh inorganic insulating layer 22e. In the present embodiment, the drain electrode 63 is the third conductive layer 67 provided above the first semiconductor 61 with the sixth inorganic insulating layer 22d and the seventh inorganic insulating layer 22e interposed therebetween. The fifth to the seventh inorganic insulating layers 22c to 22e are interlayer insulating layers for insulation between layers of the first switching element Tr, and the source electrode 62 and the drain electrode 63 are provided above the first semiconductor 61 with the interlayer insulating layers interposed therebetween. The sixth and the seventh inorganic insulating layers 22d and 22e are provided with the contact holes H1 and H2. The first conductive layer 65 is exposed at the bottom of the contact hole H1. The source electrode 62 is electrically coupled to the first semiconductor 61 through the contact hole H1 and the first conductive layer 65. In the same manner, the second conductive layer 66 is exposed at the bottom of the contact hole H2. The drain electrode 63 is electrically coupled to the first semiconductor 61 through the contact hole H2 and the second conductive layer 66.

The first conductive layer 65 is provided at a portion overlapping at least the bottom of the contact hole H1 between the source electrode 62 and the first semiconductor 61, and contacts the first semiconductor 61. The second conductive layer 66 is provided at a portion overlapping at least the bottom of the contact hole H2 between the drain electrode 63 and the first semiconductor 61, and contacts the first semiconductor 61. Since the detection device 1 is provided with the first conductive layer 65 and the second conductive layer 66, the first semiconductor 61 can be restrained from being removed by an etching solution when the contact holes H1 and H2 are formed by etching. That is, in the detection device 1, the first switching elements Tr in the detection area AA and the second switching elements TrG in the peripheral area GA can be formed in the same process, so that the manufacturing cost can be reduced.

A metal material such as aluminum (Al), copper (Cu), silver (Ag), or molybdenum (Mo), or an alloy of these materials is used as the first conductive layer 65, the second conductive layer 66, and the third conductive layer 67. The first conductive layer 65 and the second conductive layer 66 only need to be made of a conductive material that restrains the etching from progressing when the contact holes H1 and H2 are formed.

The third conductive layer 67 is provided in an area overlapping the photodiode PD in the plan view. The third conductive layer 67 is also provided on the upper side of the first semiconductor 61, the first gate electrode 64A, and the second gate electrode 64B. That is, the third conductive layer 67 is provided between the first gate electrode 64A and the lower electrode 35 in the direction orthogonal to the insulating substrate 21. This configuration causes the third conductive layer 67 to have a function as a protection layer for protecting the first switching element Tr.

The second conductive layer 66 extends so as to face the third conductive layer 67 in an area not overlapping the first semiconductor 61. A fourth conductive layer 68 is provided on the upper side of the sixth inorganic insulating layer 22d in an area not overlapping the first semiconductor 61. The fourth conductive layer 68 is provided between the second conductive layer 66 and the third conductive layer 67. This configuration forms a capacitance between the second conductive layer 66 and the fourth conductive layer 68, and a capacitance between the third conductive layer 67 and the fourth conductive layer 68. The capacitances formed by the second conductive layer 66, the third conductive layer 67, and the fourth conductive layer 68 serve as a capacitance of the capacitive element Ca illustrated in FIG. 4.

A first organic insulating layer 23a is provided on the upper side of the seventh inorganic insulating layer 22e so as to cover the source electrode 62 (signal line SGL) and the drain electrode 63 (third conductive layer 67). The first organic insulating layer 23a is a planarizing layer that planarizes asperities formed by the first switching elements Tr and various types of conductive layers.

A first inorganic insulating layer 25 is provided between the first organic insulating layer 23a and the photodiode PD in the normal direction of the insulating substrate 21. The first inorganic insulating layer 25 covers an upper surface of the first organic insulating layer 23a. The lower electrode 35 of the photodiode PD is provided on the upper side of the first inorganic insulating layer 25. In other words, the first inorganic insulating layer 25 is provided between the photodiode PD and the first switching element Tr in the normal direction of the insulating substrate 21. The first inorganic insulating layer 25 is continuously provided over the partial detection areas PAA in the plan view. The first inorganic insulating layer 25 may be provided for each of the partial detection areas PAA, or may be provided over areas overlapping the photodiodes PD and areas overlapping the first switching elements Tr.

For example, an aluminum oxide ($Al_2O_3$) film, a silicon oxide (SiO) film, a silicon nitride (SiN) film, or a silicon oxynitride (SiON) film is used as the first inorganic insulating layer 25. The first inorganic insulating layer 25 is not limited to a single layer, but may be a multilayered film.

As illustrated in FIG. 7, the photodiode PD is stacked in the order of the lower electrode 35, the third semiconductor 31, and the upper electrode 34 on the first inorganic insulating layer 25 of the backplane 2.

The third semiconductor 31 is of amorphous silicon (a-Si). The third semiconductor 31 includes an i-type semiconductor 32a, a p-type semiconductor 32b, and an n-type semiconductor 32c. The i-type semiconductor 32a, the p-type semiconductor 32b, and the n-type semiconductor 32c are specific examples of the photoelectric conversion elements. In FIG. 7, the n-type semiconductor 32c, the i-type semiconductor 32a, and the p-type semiconductor 32b are stacked in the order as listed in the direction orthogonal to the surface of the insulating substrate 21. However, a reversed configuration may be employed. That is, the p-type semiconductor 32b, the i-type semiconductor 32a, and the n-type semiconductor 32c may be stacked in the order as listed.

The lower electrode 35 is the anode of the photodiode PD and is an electrode for reading the detection signal Vdet. For example, a metal material such as molybdenum (Mo) or aluminum (Al) is used as the lower electrode 35. Alternatively, the lower electrode 35 may be a multilayered film having a plurality of stacked layers of these metal materials. The lower electrode 35 may be of a light-transmitting conductive material such as indium tin oxide (ITO).

The lower electrode 35 is electrically coupled to the third conductive layer 67 through the contact hole H3 provided in the first organic insulating layer 23a and an opening 25a provided in the first inorganic insulating layer 25. The opening 25a is provided so as to communicate with the contact hole H3. The third conductive layer 67 is electrically coupled to the lower electrode 35 serving as the anode of the photodiode PD, and is provided between the photodiode PD and the first gate electrode 64A of the first switching element Tr.

The a-Si of the n-type semiconductor 32c is doped with impurities to form an n+ region. The a-Si of the p-type semiconductor 32b is doped with impurities to form a p+ region. The i-type semiconductor 32a is, for example, a non-doped intrinsic semiconductor and has lower conductivity than those of the n-type semiconductor 32c and the p-type semiconductor 32b.

The upper electrode 34 is the cathode of the photodiode PD and is an electrode for supplying the power supply signal SVS to the photoelectric conversion layer. The upper electrode 34 is a light-transmitting conductive layer of, for example, ITO. The upper electrode 34 is provided for each of the photodiodes PD on a one-by-one basis.

The eighth inorganic insulating layer 22f and the ninth inorganic insulating layer 22g are provided on the upper side of the first inorganic insulating layer 25. The eighth inorganic insulating layer 22f covers a peripheral portion of the upper electrode 34 and is provided with an opening in a position overlapping the upper electrode 34. The coupling wiring 36 is coupled to the upper electrode 34 at a portion of the upper electrode 34 not provided with the eighth inorganic insulating layer 22f. The ninth inorganic insulating layer 22g is provided on the upper side of the eighth inorganic insulating layer 22f so as to cover the upper electrode 34 and the coupling wiring 36. A second organic insulating layer 23b serving as a planarizing layer is provided on the upper side of the ninth inorganic insulating layer 22g.

The second switching elements TrG of the gate line drive circuit 15 is provided in the peripheral area GA. The second switching elements TrG and the first switching elements Tr are provided on the same insulating substrate 21. The second switching element TrG includes a second semiconductor 81, a source electrode 82, a drain electrode 83, and a gate electrode 84.

The second semiconductor 81 is of polysilicon. The second semiconductor 81 is more preferably of low-temperature polysilicon (hereinafter, referred to as low-temperature polycrystalline silicon (LTPS)). The second switching element TrG using LTPS can be produced at a process temperature of 600 degrees Celsius or lower. Therefore, circuits such as the gate line drive circuit 15 and the signal line selection circuit 16 as well as the first switching elements Tr can be formed on the same substrate. Polysilicon has higher carrier mobility than that of a-Si. Therefore, the size of the gate line drive circuit 15 in the detection device 1 can be reduced by using polysilicon as the second switching elements TrG. As a result, the area of the peripheral area GA in the detection device 1 can be reduced. The second switching element TrG using polysilicon has higher reliability than that obtained using a-Si.

The second semiconductor 81 is provided on the upper side of the third inorganic insulating layer 22a. That is, the first semiconductor 61 of the first switching element Tr is provided in a position farther away from the insulating substrate 21 than the second semiconductor 81 of the second switching element TrG in the direction orthogonal to the insulating substrate 21. This configuration allows the second semiconductor 81 formed of polysilicon and the first semiconductor 61 formed of the oxide semiconductor to be formed on the same insulating substrate 21.

The gate electrode 84 is provided above the second semiconductor 81 with the fourth inorganic insulating layer 22b interposed therebetween. The gate electrode 84 is provided in the same layer as that of the second gate electrode 64B. The second switching element TrG has what is called the top-gate structure. However, the second switching element TrG may have the dual-gate structure or the bottom-gate structure.

The source electrode 82 and the drain electrode 83 are provided on the upper side of the seventh inorganic insulating layer 22e. The source electrode 82 and the drain electrode 83 are provided in the same layer as that of the source electrode 62 and the drain electrode 63 of the first switching element Tr. Contact holes H4 and H5 are provided through from the fourth inorganic insulating layer 22b to the seventh inorganic insulating layer 22e. The source electrode 82 is electrically coupled to the second semiconductor 81 through the contact hole H4. The drain electrode 83 is electrically coupled to the second semiconductor 81 through the contact hole H5.

The contact holes H4 and H5 are formed in four of the inorganic insulating layers (fourth to seventh inorganic insulating layers 22b to 22e), and the contact holes H1 and H2 are formed in two of the inorganic insulating layers (sixth and seventh inorganic insulating layers 22d and 22e). That is, the length of the contact holes H4 and H5 in the direction orthogonal to the insulating substrate 21 is greater than that of the contact holes H1 and H2. Even in this case, the contact holes H1 and H2 and the contact holes H4 and H5 of the detection device 1 can be formed in the same process because the first switching element Tr is provided with the first conductive layer 65 and the second conductive layer 66.

The first inorganic insulating layer 25 is provided across the detection area AA and the peripheral area GA. That is, the first inorganic insulating layer 25 is provided over an area overlapping the second switching element TrG.

Each of the third switching elements TrS included in the signal line selection circuit 16 illustrated in FIG. 3 may have the same configuration as that of the second switching element TrG. That is, the semiconductor of the third switching element TrS is of polysilicon, and is more preferably of LTPS. In this case, the circuit scale of the signal line selection circuit 16 of the detection device 1 can be reduced. The semiconductor of the third switching element TrS is not limited to such materials, but may be an oxide semiconductor including a TAOS. In the same manner, each of the fourth switching elements TrR included in the reset circuit 17 illustrated in FIG. 3 may also have the same configuration as that of the second switching element TrG. That is, the semiconductor of the fourth switching elements TrR is of polysilicon, and is more preferably of LTPS. In this case, the circuit scale of the reset circuit 17 of the detection device 1 can be reduced. The semiconductor of the fourth switching elements TrR is not limited to such materials but may be an oxide semiconductor including a TAOS.

The terminal portion 72 is provided in a position of the peripheral area GA different from the area provided with the gate line drive circuit 15. The terminal portion 72 includes a first terminal conductive layer 73, a second terminal conductive layer 74, a third terminal conductive layer 75, and a fourth terminal conductive layer 76. The first terminal conductive layer 73 is provided in the same layer as that of the second gate electrode 64B and on the fourth inorganic insulating layer 22b. A contact hole H6 is provided so as to extend through the fifth inorganic insulating layer 22c, the sixth inorganic insulating layer 22d, the seventh inorganic insulating layer 22e, and the first organic insulating layer 23a.

The second terminal conductive layer 74, the third terminal conductive layer 75, and the fourth terminal conductive layer 76 are stacked in the contact hole H6 in the order as listed and are electrically coupled to the first terminal conductive layer 73. The second terminal conductive layer 74 can be formed using the same material as and in the same process as those of the third conductive layer 67 and the like. The third terminal conductive layer 75 can be formed using the same material as and in the same process as those of the lower electrode 35. The fourth terminal conductive layer 76 can be formed using the same material as and in the same process as those of the coupling wiring 36 and the power supply signal line Lvs (refer to FIG. 6).

Although FIG. 7 illustrates one terminal portion 72, a plurality of such terminal portions 72 are arranged with gaps interposed therebetween. The terminal portions 72 are electrically coupled to the flexible printed circuit board 71 (refer to FIG. 1) through, for example, an anisotropic conductive film (ACF).

As described above, the detection device 1 of the present embodiment includes the insulating substrate 21, the photoelectric conversion elements (photodiodes PD) that are arranged in the detection area AA of the insulating substrate 21 and each output the signal corresponding to the light emitted thereto, the first switching elements Tr that are provided corresponding to the photoelectric conversion elements and each include the first semiconductor 61, the source electrode 62, and the drain electrode 63, and the first inorganic insulating layer 25 provided between the photoelectric conversion elements and the first switching elements Tr in the normal direction of the insulating substrate 21.

This configuration allows the first inorganic insulating layer 25 to restrain hydrogen (H) generated from the photodiode PD from being diffused to the first switching element Tr. That is, the first inorganic insulating layer 25 serves as a barrier layer that reduces permeation of hydrogen (H). Hydrogen (H) is generated from the photodiode PD, for example, when the third semiconductor 31 of amorphous silicon (a-Si) is formed into a film, and when the lower electrode 35 formed of ITO is treated with heat. Thus, in the detection device 1, it is possible to reduce changes in characteristics of, for example, the first semiconductor 61 of the first switching element Tr that would be caused by the diffusion of hydrogen (H) so as to ensure reliability.

The detection device 1 of the present embodiment also includes the planarizing film (first organic insulating layer 23a) covering the first switching element Tr, and the first inorganic insulating layer 25 is provided between the planarizing film and the photoelectric conversion element in the normal direction of the insulating substrate 21.

This configuration allows the first inorganic insulating layer 25 to reduce an influence on the planarizing film in the manufacturing process of the photodiode PD. Although the configuration has been described in which amorphous silicon (a-Si) is used as the photodiode PD, the configuration is not limited thereto. An organic material may be used for the photodiode PD. Even in this case, the first inorganic insulating layer 25 prevents the organic material of the photodiode PD from contacting the first organic insulating layer 23a, so that the influence on the planarizing film can be reduced in the manufacturing process of the photodiode PD.

In the detection device 1 of the present embodiment, the source electrode 62 and the drain electrode 63 are provided above the first semiconductor 61 with the interlayer insulating layers (the sixth inorganic insulating layer 22d and the seventh inorganic insulating layer 22e) interposed therebetween, and are electrically coupled to the first semiconductor 61 through the contact holes H1 and H2, respectively, provided in the interlayer insulating layers. The planarizing film covers the source electrode 62 and the drain electrode 63. That is, the first inorganic insulating layer 25 is provided in a layer different from the interlayer insulating layers included in the first switching element Tr, and serves as the barrier layer that reduces the permeation of hydrogen (H).

In the detection device 1 of the present embodiment, the first inorganic insulating layer 25 is provided over the area overlapping the second switching element TrG. Thus, in the detection device 1, it is possible to reduce changes in characteristics of the second switching elements TrG that would be caused by the diffusion of hydrogen (H).

Second Embodiment

Figure 8:
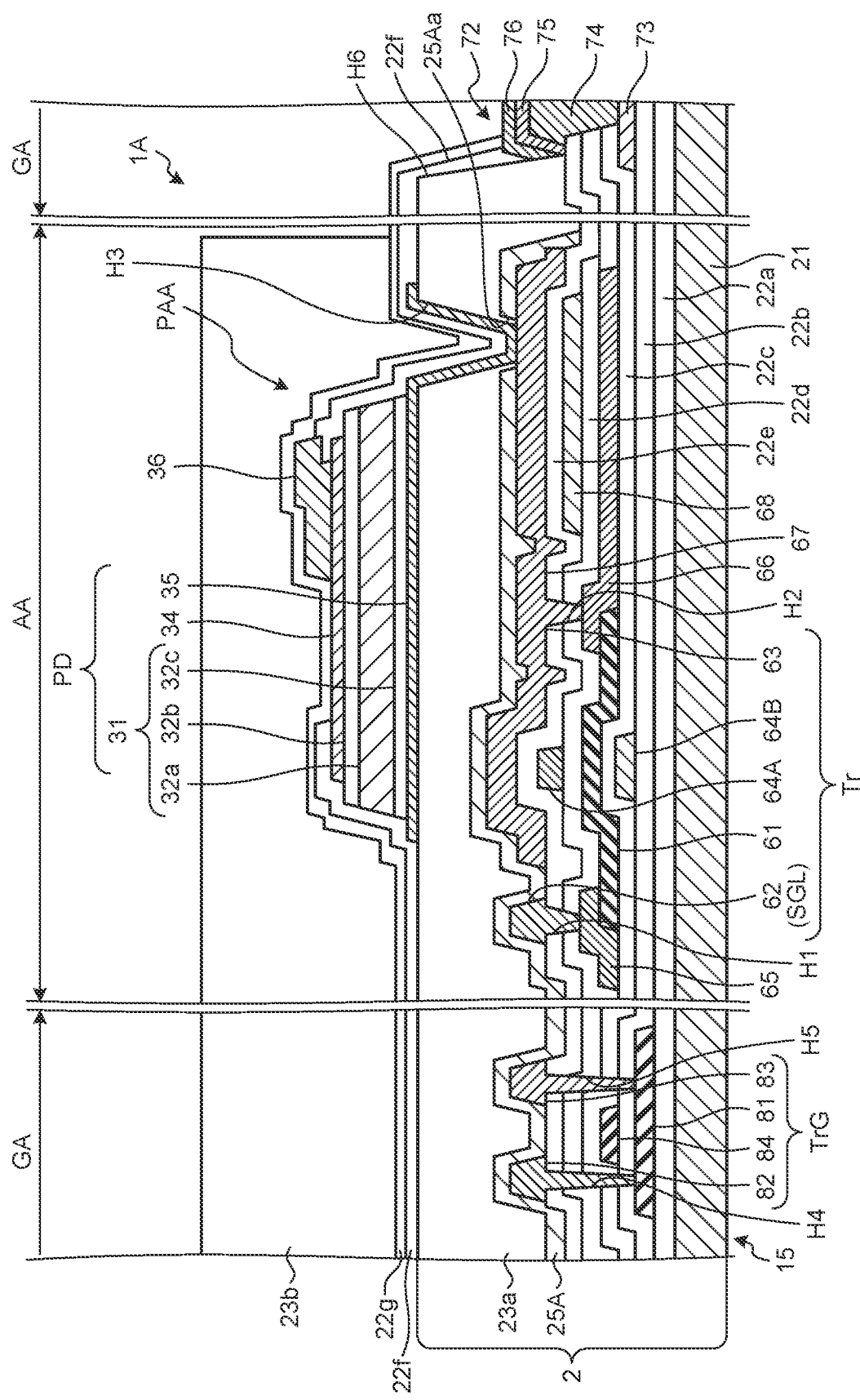
FIG. 8 is a sectional view illustrating a schematic sectional configuration of a detection device according to a second embodiment.

FIG. 8 is a sectional view illustrating a schematic sectional configuration of a detection device according to a second embodiment. In the following description, the components described in the above-described embodiment will be denoted by the same reference numerals and will not be described.

As illustrated in FIG. 8, in a detection device 1A of the present embodiment, a second inorganic insulating layer 25A is provided instead of the first inorganic insulating layer 25. The second inorganic insulating layer 25A is provided between the first organic insulating layer 23a and the first switching element Tr in the normal direction of the insulating substrate 21. Specifically, the second inorganic insulating layer 25A is provided on the upper side of the seventh inorganic insulating layer 22e so as to cover the source electrode 62 (signal line SGL) and the drain electrode 63 (third conductive layer 67). The lower electrode 35 of the photodiode PD is provided on the upper side of the first organic insulating layer 23a.

Also in the present embodiment, the second inorganic insulating layer 25A can restrain the hydrogen (H) generated from the photodiode PD from permeating the first switching element Tr.

The second inorganic insulating layer 25A is provided over the area overlapping the second switching element TrG and covers the source electrode 82 and the drain electrode 83. This configuration can restrain the hydrogen (H) generated from the photodiode PD from permeating the second switching element TrG.

Third Embodiment

Figure 9:
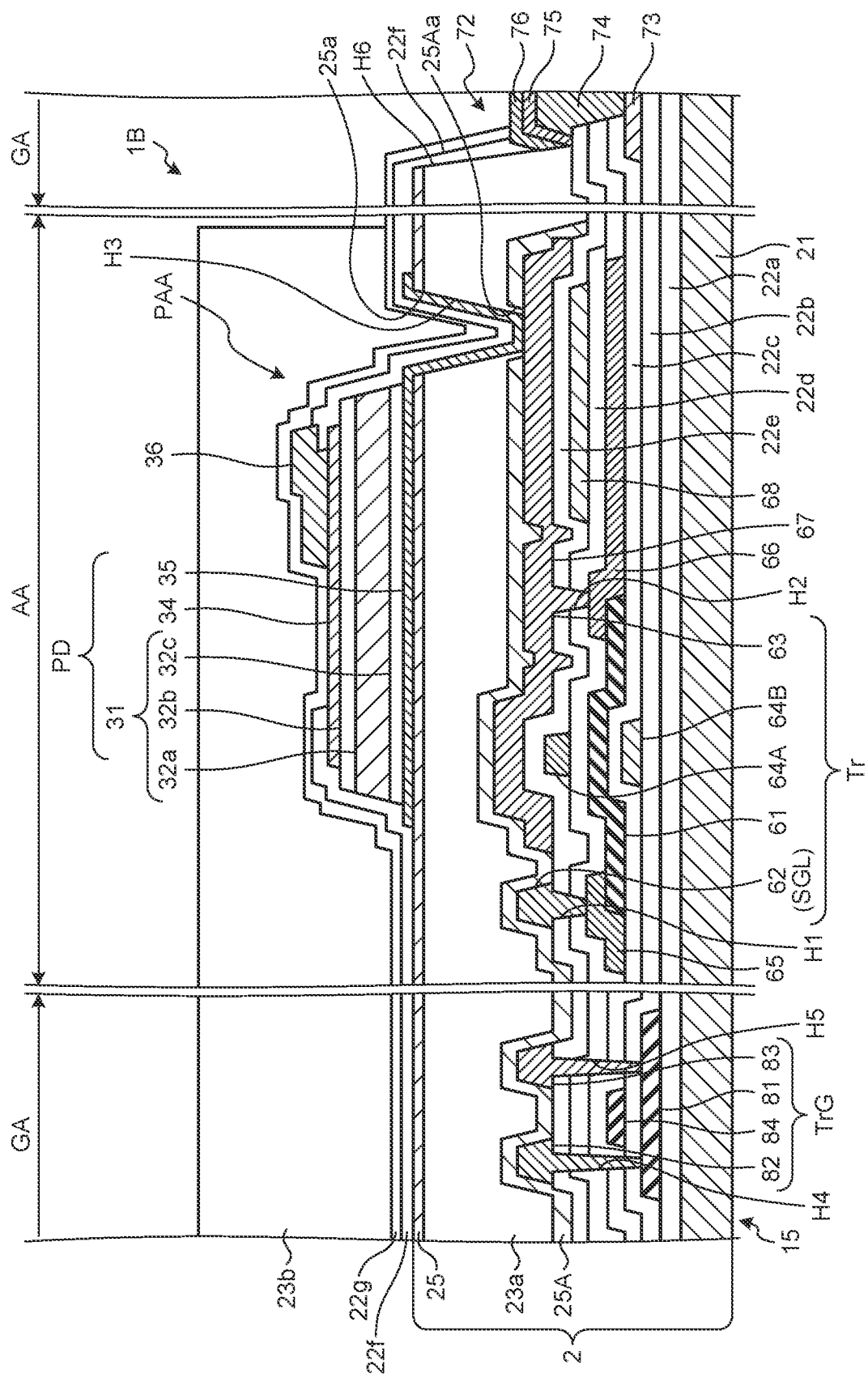
FIG. 9 is a sectional view illustrating a schematic sectional configuration of a detection device according to a third embodiment.

FIG. 9 is a sectional view illustrating a schematic sectional configuration of a detection device according to a third embodiment. As illustrated in FIG. 9, in a detection device 1B of the present embodiment, the second inorganic insulating layer 25A is provided in addition to the first inorganic insulating layer 25. The first inorganic insulating layer 25 is provided between the first organic insulating layer 23a and the photodiode PD in the normal direction of the insulating substrate 21. The second inorganic insulating layer 25A is provided between the first organic insulating layer 23a and the first switching element Tr. Specifically, the second inorganic insulating layer 25A covers the source electrode 62 (signal line SGL) and the drain electrode 63 (third conductive layer 67) of the first switching element Tr. The first organic insulating layer 23a is disposed so as to be sandwiched between the first inorganic insulating layer 25 and the second inorganic insulating layer 25A in the normal direction of the insulating substrate 21.

Also in the present embodiment, the first inorganic insulating layer 25 and the second inorganic insulating layer 25A can restrain the hydrogen (H) generated from the photodiode PD from permeating the first switching element Tr. This configuration can increase the effect of blocking the hydrogen (H) generated from the photodiode PD to a higher level than that of the first and the second embodiments. The first inorganic insulating layer 25 and the second inorganic insulating layer 25A are also provided in the peripheral area GA and are provided over the area overlapping the second switching element TrG.

Fourth Embodiment

Figure 10:
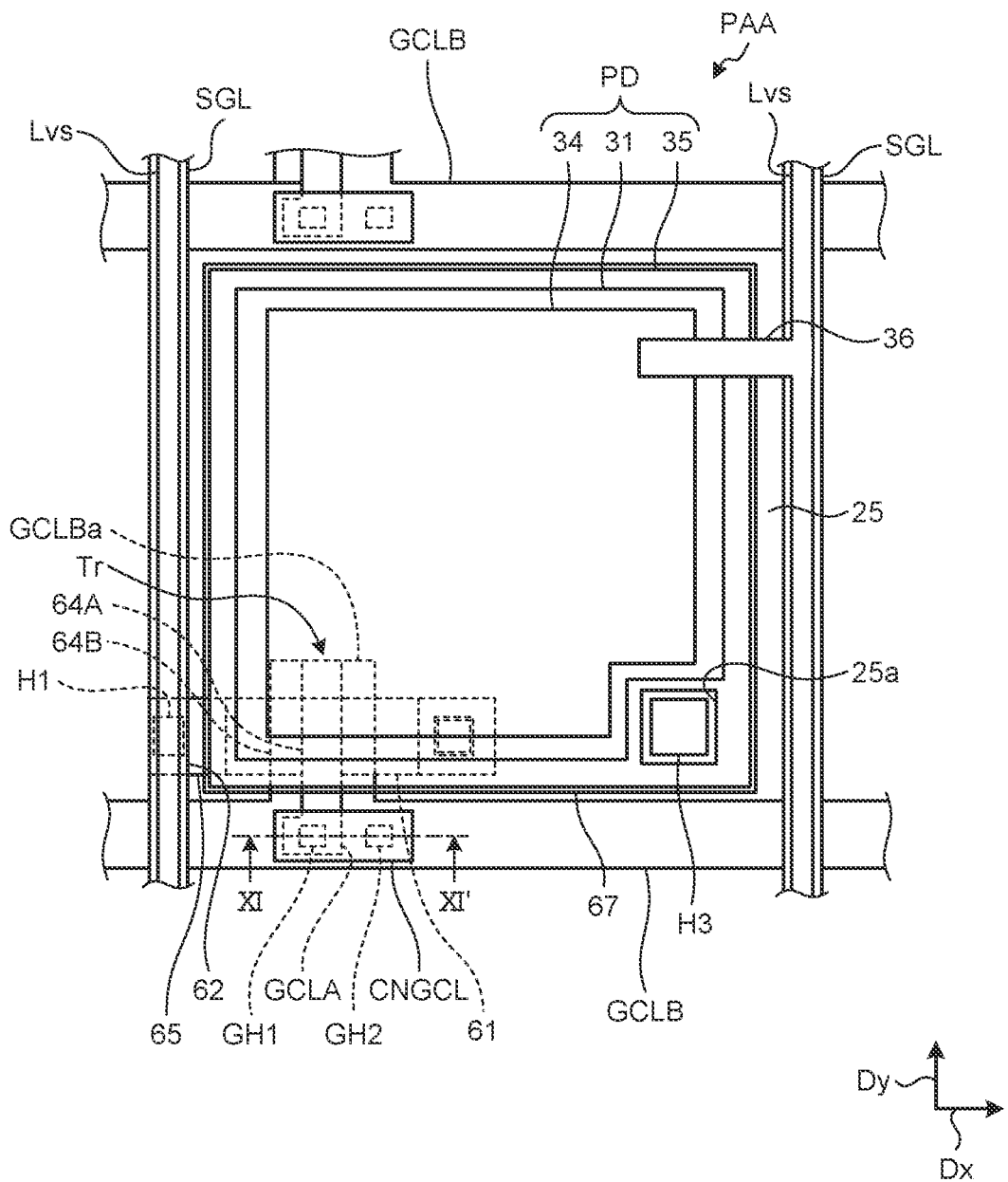
FIG. 10 is a plan view schematically illustrating the partial detection area of a detection device according to a fourth embodiment.
Figure 11:
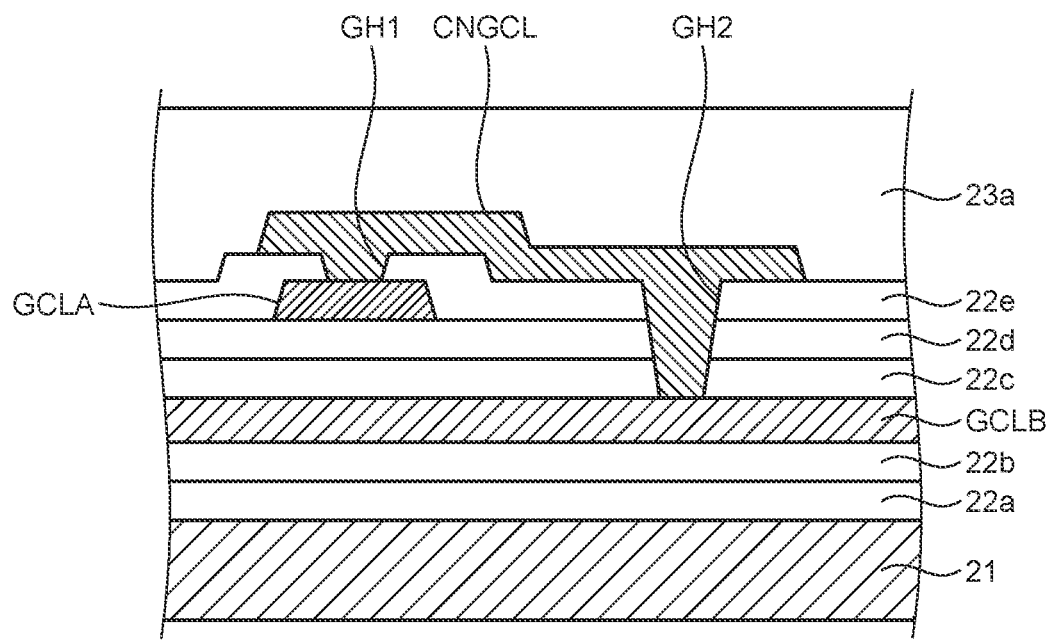
FIG. 11 is a sectional view taken along line XI-XI' of FIG. 10.

FIG. 10 is a plan view schematically illustrating the partial detection area of a detection device according to a fourth embodiment. FIG. 11 is a sectional view taken along line XI-XI' of FIG. 10. As illustrated in FIG. 10, the first gate line GCLA (first gate electrode 64A) is electrically coupled to the second gate line GCLB (second gate electrode 64B) in an area surrounded by the second gate lines GCLB and the signal lines SGL. The area surrounded by the second gate lines GCLB and the signal lines SGL includes an area overlapping the second gate line GCLB between the adjacent signal lines SGL.

Specifically, the first gate line GCLA extends in the second direction Dy, and the second gate line GCLB extends in the first direction Dx. A second gate line branch portion GCLBa branches from the second gate line GCLB and extends in the second direction Dy. The first gate line GCLA is provided so as to overlap the second gate line branch portion GCLBa. A gate line coupling layer CNGCL is provided so as to overlap portions of the first gate line GCLA and the second gate line GCLB.

As illustrated in FIG. 11, the second gate line GCLB is provided on the upper side of the fourth inorganic insulating layer 22b. The first gate line GCLA is provided on the upper side of the sixth inorganic insulating layer 22d. The gate line coupling layer CNGCL is provided on the upper side of the seventh inorganic insulating layer 22e. The first gate line GCLA is coupled to the gate line coupling layer CNGCL through a contact hole GH1 provided in the seventh inorganic insulating layer 22e. The second gate line GCLB is coupled to the gate line coupling layer CNGCL through a contact hole GH2 provided so as to penetrate from the fifth inorganic insulating layer 22c to the seventh inorganic insulating layer 22e. This configuration electrically couples the first gate line GCLA to the second gate line GCLB through the gate line coupling layer CNGCL.

In the present embodiment, the first gate line GCLA (first gate electrode 64A) is electrically coupled to the second gate line GCLB (second gate electrode 64B) in each of the partial detection areas PAA. Thus, the difference between a voltage applied to the first gate electrode 64A and a voltage applied to the second gate electrode 64B can be lowered as compared with the configuration in which the first gate line GCLA is electrically coupled to the second gate line GCLB in the peripheral area GA.

Fifth Embodiment

Figure 12:
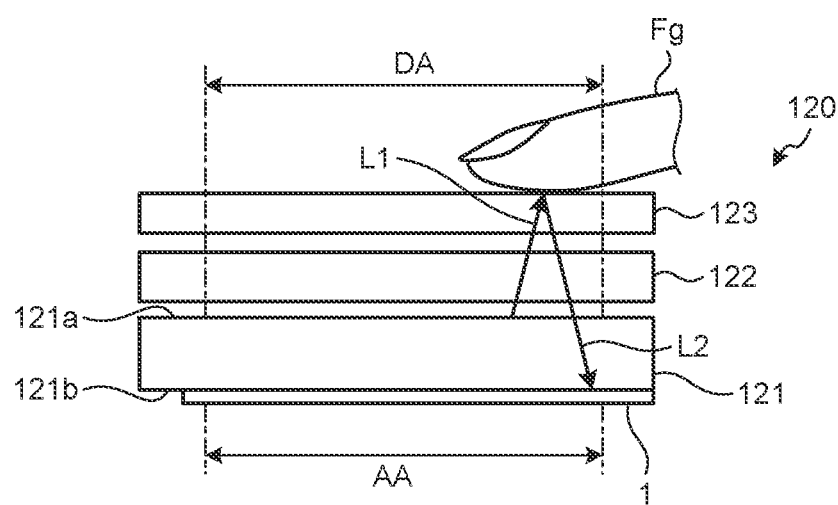
FIG. 12 is a sectional view illustrating a schematic sectional configuration of a display device according to a fifth embodiment.

FIG. 12 is a sectional view illustrating a schematic sectional configuration of a display device according to a fifth embodiment. As illustrated in FIG. 12, a display device 120 includes the detection device 1, a display panel 121, a touchscreen panel 122, and a cover glass 123. The display panel 121 may be, for example, an organic electroluminescent (EL) (organic light-emitting diode (OLED)) display panel or an inorganic EL (micro-LED or mini-LED) display panel using light-emitting elements as the display elements. Alternatively, a display panel 121 may be a liquid crystal display (LCD) panel that uses liquid crystal elements as the display elements, or an electrophoretic display (EPD) panel that uses electrophoretic elements as the display elements. Although the amorphous silicon material is used as the photoelectric conversion elements used in the detection device 1, an organic material, for example, may instead be used.

The display panel 121 has a first principal surface 121a and a second principal surface 121b that is a side opposite to the first principal surface 121a. The first principal surface 121a is a surface that emits light L1 from display elements toward the cover glass 123 to display an image. The first principal surface 121a has a display area DA in which the image is displayed.

The touchscreen panel 122 uses, for example, a capacitance method to detect a finger Fg in contact with or in proximity to a surface of the cover glass 123. The touchscreen panel 122 is transmissive of light and can transmit the light L1 and light L2 that has been reflected on an interface between the cover glass 123 and air. The display device 120 may have a configuration not including the touchscreen panel 122. The display panel 121 may be integrated with the touchscreen panel 122 or may incorporate functions of the touchscreen panel 122.

The cover glass 123 is a member for protecting, for example, the display panel 121 and covers, for example, the display panel 121. The cover glass 123 is, for example, a glass substrate. The present disclosure is not limited to using the cover glass 123. For example, a resin substrate may be provided above the touchscreen panel 122.

The detection device 1 is provided so as to face the second principal surface 121b of the display panel 121. The detection device 1 can detect the asperities of the surface of the finger Fg by detecting the light L2 reflected on the interface between the cover glass 123 and air. Since the detection device 1 can be easily increased in area, the detection area AA of the detection device 1 is provided so as to face the entire display area DA of the display panel 121. The detection area AA is not limited to this configuration. The detection area AA may face a portion of the display area DA of the display panel 121.

While the preferred embodiments of the present disclosure have been described above, the present disclosure is not limited to the embodiments described above. The content disclosed in the embodiments is merely an example, and can be variously modified within the scope not departing from the gist of the present disclosure. Modifications appropriately made within the scope not departing from the gist of the present disclosure naturally belong to the technical scope of the present disclosure.

For example, each of the detection devices 1, 1A, and 1B is not limited to the case of being used as the fingerprint sensor for detecting the fingerprint of the finger Fg. Each of the detection devices 1, 1A, and 1B can be used as a biosensor that detects various types of biological information such as a blood vessel image of the finger Fg or the palm, a pulse wave, pulsation, and a blood oxygen concentration.

What is claimed is:

1. A detection device comprising:
    an insulating substrate;
    a plurality of photoelectric conversion elements that are arranged in a detection area of the insulating substrate, and each of which is configured to receive light and output a signal corresponding to the received light;
    a first switching element that is provided for each photoelectric conversion element and comprises a first semiconductor, a source electrode, and a drain electrode;
    an inorganic insulating layer provided between the photoelectric conversion element and the first switching element in a normal direction of the insulating substrate; and
    a planarizing film that covers the first switching element, wherein
    the inorganic insulating layer comprises a first inorganic insulating layer and a second inorganic insulating layer, and
    the first inorganic insulating layer is provided between the planarizing film and the photoelectric conversion element in the normal direction of the insulating substrate.

2. The detection device according to claim 1, wherein the second inorganic insulating layer is provided between the planarizing film and the first switching element in the normal direction of the insulating substrate.

3. The detection device according to claim 2, wherein
    the source electrode and the drain electrode are provided above the first semiconductor with an interlayer insulating layer interposed between the source and drain electrodes and the first semiconductor, and each of the source electrode and the drain electrode is electrically coupled to the first semiconductor through a contact hole provided in the interlayer insulating layer, and
    the inorganic insulating layer covers the source electrode and the drain electrode.

4. The detection device according to claim 1, further comprising:
    a plurality of gate lines coupled to the first switching elements and extending in a first direction; and
    a gate line drive circuit that comprises a second switching element comprising a second semiconductor, is provided in a peripheral area outside the detection area, and is configured to drive the gate lines, wherein
    the inorganic insulating layer is provided over an area overlapping the second switching element.

5. The detection device according to claim 4, wherein
    the first semiconductor is an oxide semiconductor, and
    the second semiconductor is of polysilicon.

6. The detection device according to claim 1, wherein
    the source electrode and the drain electrode are provided above the first semiconductor with an interlayer insulating layer interposed between the source and drain electrodes and the first semiconductor, and each of the source electrode and the drain electrode is electrically coupled to the first semiconductor through a contact hole provided in the interlayer insulating layer, and
    the second inorganic insulating layer covers the source electrode and the drain electrode.

7. The detection device according to claim 1, wherein
    the first switching element comprises a first gate electrode and a second gate electrode provided with the first semiconductor interposed therebetween in the normal direction of the insulating substrate,
    the detection device further comprises:
        a plurality of gate lines coupled to the first switching elements and extending in a first direction; and
        a plurality of signal lines coupled to the first switching elements and intersecting the first direction, and
    the first gate electrode is electrically coupled to the second gate electrode in an area surrounded by the gate lines and the signal lines.

8. A display device comprising:
    the detection device according to claim 1; and
    a display panel that comprises display elements to display an image and is disposed so as to face the detection device.

9. The detection device according to claim 1, wherein
    the photoelectric conversion elements further includes a lower electrode, and
    the first inorganic insulating layer is disposed between the lower electrode and the planarizing film in the normal direction of the insulating substrate.

* * * * *